United States Patent
Mullor Torres et al.

(10) Patent No.: US 8,247,645 B2
(45) Date of Patent: Aug. 21, 2012

(54) METHOD FOR PROVIDING CUCUMBER FRUITS WITH AN EXTENDED SHELF LIFE

(75) Inventors: Luis Mullor Torres, Aguadulce (ES); Nanne Machiel Faber, SJ Hoorn (NL); Jacob Pieter Mazereeuw, HB Enkhuizen (NL); Johannes Jacobus Maria Lambalk, MG Middenbeemster (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 997 days.

(21) Appl. No.: 12/083,211

(22) PCT Filed: Oct. 7, 2005

(86) PCT No.: PCT/EP2005/055107
§ 371 (c)(1),
(2), (4) Date: May 15, 2008

(87) PCT Pub. No.: WO2007/042070
PCT Pub. Date: Apr. 19, 2007

(65) Prior Publication Data
US 2010/0170001 A1    Jul. 1, 2010

(51) Int. Cl.
*A01H 1/04* (2006.01)
*A01H 5/00* (2006.01)
*A01H 5/08* (2006.01)
(52) U.S. Cl. .................. 800/267; 800/266; 800/307
(58) Field of Classification Search .................. None
See application file for complete search history.

(56) References Cited

FOREIGN PATENT DOCUMENTS

| EP | 1 188 833 A1 | 3/2002 |
| EP | 1188833 A1 * | 3/2002 |
| JP | 2004 321055 | 11/2004 |

OTHER PUBLICATIONS

Fazio et al., "Genetic mapping and QTL analysis of horticultural traits in cucumber (*Cucumis sativus* L.) using recombinant inbred lines," Theor. Appl. Genet. 107: 864-874 (2003).
Kanellis et al., "Effect of Stage of Development on Postharvest Behavior of Cucumber Fruit," HortScience 21(5): 1165-1167 (1986).
Wehner, et al., "Screening the Cucumber Germplasm Collection for Fruit Storage Ability," HortScience 35(4): 699-707 (2000).

* cited by examiner

*Primary Examiner* — David T Fox
*Assistant Examiner* — Keith Robinson
(74) *Attorney, Agent, or Firm* — The Nath Law Group; Joshua B. Goldberg; Tanya E. Harkins

(57) ABSTRACT

A method for producing a *Cucumis sativus* plant, providing cucumber fruits exhibiting "extended shelf life, comprising: (a) providing a first *Cucumis sativus* plant containing at least one quantitative trait locus (QTL); (b) crossing the first plant with a second *Cucumis sativus* plant; (c) analyzing the progeny for presence or absence of QTL; and (d) identifying and selecting plants containing QTL. The QTL is selected from QTL1 or QTL2. QTL1 has a first molecular marker of SEQ ID No:1, a cucumber genomic fragment, and SEQ ID No:2, and a second molecular marker of SEQ ID No:3, a cucumber genomic fragment, and SEQ ID No:4. QTL2 has a first molecular marker of SEQ ID No:5, a cucumber genomic fragment, and SEQ ID No:6, and a second molecular marker of SEQ ID No:7, a cucumber genomic fragment, and SEQ ID No:8.

13 Claims, 1 Drawing Sheet

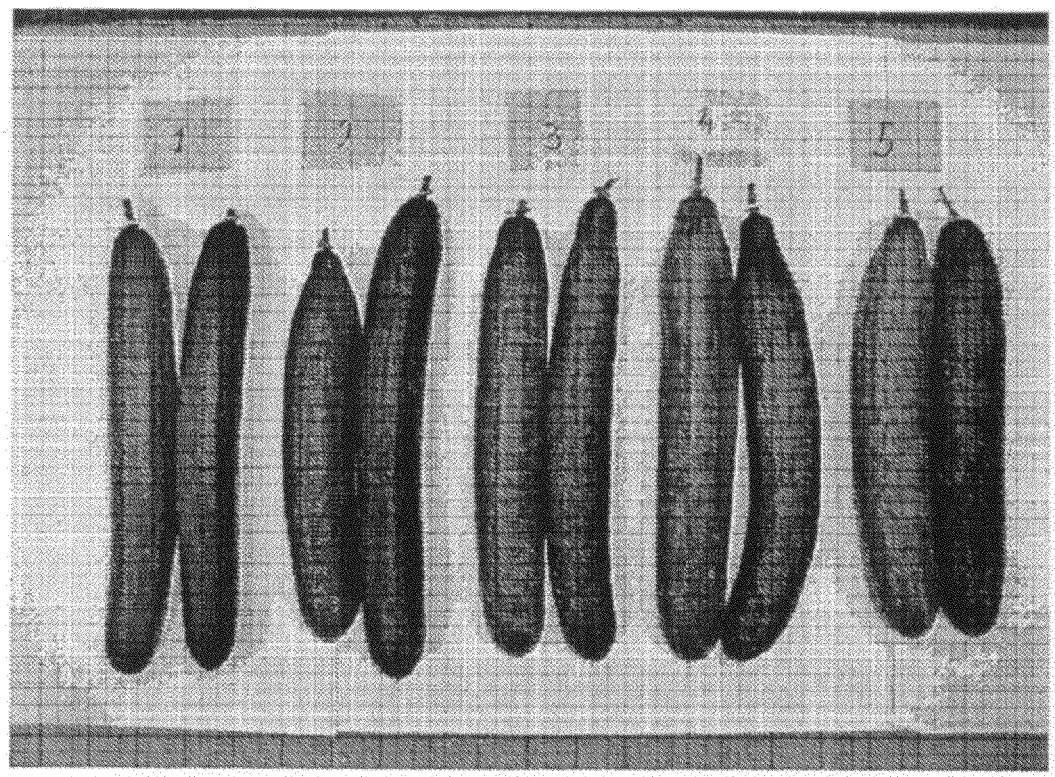

METHOD FOR PROVIDING CUCUMBER FRUITS WITH AN EXTENDED SHELF LIFE

The present invention relates to a method for producing a *Cucumis sativus* plant, providing cucumber fruits exhibiting the phenotypic trait "extended shelf life". The invention further relates to the plants obtainable by said method, and to the seeds and cucumber fruits thereof. In addition, the invention relates to molecular markers for use in the method of the invention, and to the use thereof for identifying plants having an extended shelf life.

Cucumbers are the edible fruits of the cucumber plant *Cucumis sativus*, which belongs to the gourd family Cucurbitaceae like melons and squash. It is a long, green-skinned fruit, which consists of about 96% water. The cucumber plant, which has been cultivated since long, is an important horticultural crop in Europe, America and much of Asia. The cucumber fruits are commonly harvested while still green and are generally used for both the pickling industry and the fresh market, which latter usage has the greatest added value for the farmers. Due to its relatively short shelf life, storage and shipping of fresh cucumber fruits is, however, difficult and expensive. Cooling, which is generally used to extend the shelf life of fresh products, cannot be applied for cucumber fruits as these fruits are not suitable for storage at low temperatures.

It is known to extend the shelf life of cucumber fruits by for example wrapping them in sealing foil or storing them under controlled conditions (>10° C.). However, additional processing steps or specific storage measures thus have to be taken. In addition, in this way the shelf life is extended only in the specific cucumbers that have been wrapped in foil, or have, been stored under said specific conditions.

Accordingly, there is a need for cucumber fruits having a longer shelf life under standard storage and transport conditions.

The object of the present invention is to provide a method for producing plants providing cucumber fruits that can be maintained for a longer period of time compared to conventional cucumber fruits under the same standard storage and transport conditions.

This is achieved by the invention by a method for producing a *Cucumis sativus* plant, providing cucumber fruits exhibiting the phenotypic trait "extended shelf life", comprising:

(a) providing a first *Cucumis sativus* plant comprising at least one quantitative trait loci (QTL) associated with said phenotypic trait;

(b) crossing the plant provided in step (a) with a second *Cucumis sativus* plant;

(c) analyzing the progeny of the cross of step (b) for the presence or absence of at least one QTL; and (d) identifying and selecting from the progeny thereof plants containing the at least one QTL;

wherein the at least one QTL is selected from QTL1 and QTL2, and wherein:

QTL1 is identified by a first molecular marker of about 66 base pairs consisting from 5' to 3': of a first primer having the nucleotide sequence GACTGCGTAC CAATTCTT SEQ ID No:1, a cucumber genomic fragment, and a second primer having the nucleotide sequence GATGAGTCCT GAGTAACAT SEQ ID No:2, and a second molecular marker of about 230 base pairs consisting from 5' to 3': of a first primer having a nucleotide sequence GACTGCGTAC CAATTCCC SEQ ID No.: 3, a cucumber genomic fragment, and a second primer having the nucleotide sequence GATGAGTCCT GAGTAACAT SEQ ID No: 4,; or any part of the DNA sequence between the first and second marker;

QTL2 is identified by a first molecular marker of about 137 base pairs consisting from 5' to 3': of a first primer having the nucleotide sequence GACTGCGTAC CAATTCAT SEQ ID No:5, a cucumber genomic fragment, and a second primer having the nucleotide sequence GATGAGTCCT GAGTAACAT SEQ ID No:6, and a second molecular marker of about 230 base pairs consisting from 5' to 3': of a first primer having a nucleotide sequence GACTGCGTAC CAATTCTA SEQ ID No.: 7, a cucumber genomic fragment, and a second primer having the nucleotide sequence GATGAGTCCT GAGTAACTA SEQ ID No: 8; or any part of the DNA sequence between the first and second marker.

With the method of the present invention, cucumber plants that provide cucumber fruits having an extended shelf life can be easily identified and selected from a population of plants and for example further be used in marker-assisted breeding programs. It is not necessary to wait for the cucumber fruits to be present in order to identify and select the plants. It will be clear that the method of the invention will lead to a reduction in time, labour, greenhouse space, and ultimately costs, needed for producing cucumber fruits having the desired phenotypic trait.

In the research that led to the present invention two quantitative trait loci (QTLs) were identified in the genome of the cucumber plant that were found to be associated with the phenotypic trait of extended shelf life of the cucumber fruits provided by the plant. A quantitative trait locus (QTL) is a region of DNA that is closely linked to a specific phenotypic trait.

The presence of the QTLs was inferred from genetic mapping, i.e. QTL mapping. Because most of the traits of interest, including the present trait, are governed by more than one gene (a phenomenon called epistasis), statistical analysis generally is required to demonstrate that different genes interact with one another and to determine whether they produce a significant effect on the phenotype. In the research that led to the present invention, two QTLs were found. These QTLs are identifiable by molecular markers, i.e.

identifiable physical locations in the genome. The QTLs of the present invention are identified by specific molecular markers, i.e. amplified fragment length polymorphisms (AFLP). Preferably, the QTLs are identified by at least two flanking molecular markers. The term "molecular marker" thus refers to a specific DNA fragment which is associated with the QTL which contributes to a specific phenotypic trait.

According to a preferred embodiment of the invention at least one of the QTLs is present, preferably the at least one QTL is QTL1.

In a particularly preferred embodiment of the invention, QTL1 is defined by the nucleotide sequence

```
                                                    SEQ ID No: 9
GATAACCTTC TTTCCAAGGT TTGCACTAAT GTTTCTCTTT

TGCTTGTAAT TGATGGTTGC CTCTCTTTTT TATTCTTCTC

TTTTCTTTTT TGGAGGGGCC TGGGATGAGC AAATGTACTT

GGTAATCTGA AAATTTTGAG GAACTAAAAC TAAAGAGCAA

TTATCCCTTT CCACGAATAC TTTTTTTTGC TAAATTCTGG

ATCTCTTCAT GGATTTTAAC CAAGGAAATA GTTGTATCGA

TTAATTCTTA GTTTACTTTA ATCCCTCGGC TATTAATTGC

CACTTTAATG TCTAAACAAG GAACTAAATT AGTCTTAGAA

GTTCCATGTA TCATATACAT GAATGATGCA TTAATAGATC

TGTTCTCTAT ATTGTATTGG AATTGGCGCT TTTTC.
```

In a further preferred embodiment, both QTL1 and QTL2 are present. When both QTLs are present the longest shelf life is obtained.

According to the present invention the genetic control of the quality trait extended shelf life has been determined and specific markers have been developed which can be used for further (marker-assisted) breeding programs for cucumber fruits with long shelf life.

As used throughout this application, the term "shelf life" relates to the period of time (in days) wherein a tolerable loss in quality of the cucumber fruits occurs, i.e. the time period after harvesting the cucumber fruits up to which the loss in quality of the cucumber fruits becomes intolerable for consumers.

The phenotypic trait of shelf life may e.g. be related to the colour of the cucumber fruit. After harvest the colour of the cucumber fruit will be green, which colour will change gradually in time to lighter green and yellow. In FIG. 1 five cucumbers are shown: (1) Good colour (green); (2) Acceptable colour (somewhat lighter green); (3) Unacceptable colour (first occurrence of yellowing); (4) Unacceptable colour (yellowing); (5) Unacceptable colour (extreme yellowing). In the present invention the shelf life of the cucumber fruit is defined by the amount of days between harvest of the cucumber fruit and the moment the colour of the cucumber fruit reaches stage (3), i.e. the moment the first yellowing occurs.

According to a preferred embodiment of the invention, the phenotypic trait "an extended shelf life" corresponds to a shelf life which is extended by at least two, preferably at least four, more preferably at least six days, as compared to the shelf life of cucumber fruits not containing the QTLs, when stored under the same storage conditions, i.e. storage of unwrapped cucumbers in plastic boxes in a conditioned dark cell, at 20' C., 80% humidity.

Conventional cucumber fruits, when stored under such storage conditions generally have an average shelf life of 16 days. The shelf life of the cucumber fruits according to the present invention under standard conditions is at least 18 days, preferably at least 20 days, more preferably at least 22 days.

The present invention further relates to Cucumber *sativus* plants, obtainable by the method as described above, as well as to seeds and progeny derived from such plant. The term "progeny" may refer to the descendants of a particular plant (self-pollination) or pair of plants (cross-pollinated). The descendants can for example be of the F1, F2 or subsequent generation, wherein F1 and F2 is the shorthand notation used to denote the different generations involved in breeding. F1 is the first generation, i.e. the progeny of a parental cross; F2 is the second generation, i.e. the progeny of self-fertile or intercrossing F1 individuals and so on.

In addition, the invention relates to cucumber fruits having an extended shelf life, which are provided by said *Cucumis sativus* plant or by the progeny thereof, or by a *Cucumis sativus* plant regenerated from seed of said plants.

Moreover, the present invention relates to a molecular marker for use in the method as described above. The invention in particular relates to a the following molecular markers:
a molecular marker of about 66 base pairs consisting from 5' to 3' of a first primer having the nucleotide sequence SEQ ID No:1, a cucumber genomic fragment, and a second primer having the nucleotide sequence SEQ ID No:2;
a molecular marker of about 230 base pairs consisting from 5' to 3' of a first primer having the nucleotide sequence SEQ ID No:3, a cucumber genomic fragment, and a second primer having the nucleotide sequence SEQ ID No:4;
a molecular marker of about 137 base pairs consisting from 5' to 3' of a first primer having the nucleotide sequence SEQ ID No:5, a cucumber genomic fragment, and a second primer having the nucleotide sequence SEQ ID No:6;
a molecular marker of about 230 base pairs consisting from 5' to 3' of a first primer having the nucleotide sequence SEQ ID No:7, a cucumber genomic fragment, and a second primer having the nucleotide sequence SEQ ID No:8.

The invention also relates to the use of said DNA-markers for identifying a *Cucumis sativus* plant providing cucumber fruits exhibiting the phenotypic trait "extended shelf life". The plant thus identified can e.g. further be used in marker-assisted breeding of cucumber fruit plants having an extended shelf life.

The invention is further illustrated by the following Examples.

FIG. 1 shows the gradual change in time of the colour of cucumbers from green to lighter green and yellow: (1) Good colour (green); (2) Acceptable colour (somewhat lighter green); (3) Unacceptable colour (first occurrence of yellowing); (4) Unacceptable colour (yellowing); (5) Unacceptable colour (extreme yellowing).

EXAMPLES

Example 1

A parental line with the phenotypic trait extended shelf life was crossed with a cucumber plant not having said phenotypic trait. F1 seeds were harvested and used for the production of a segregating population according to well-known standard methods. The population was sown in the greenhouse and cucumber fruits were obtained. The colour of the cucumber fruits was measured during storage as described above.

The population was used for QTL analysis using the AFLP technology, i.e. a highly sensitive method for detecting polymorphisms in DNA, wherein following restriction enzyme digestion of DNA, a subset of DNA fragments are selected for PCR amplification and visualisation.

A first major QTL, QTL1, was identified in a 17 cM interval (measured in the DH population), explaining 29% of the phenyptic trait "extended shelf life". A second QTL, QTL2, was identified in a 34 CM interval explaining 11% of the desired phenotype.

Using the identified AFLP-markers the genomic sequence of QTL1 was identified (SEQ ID No: 9). According to the invention it has been demonstrated that cucumber plants, in which SEQ ID No: 9 is present, exhibit the phenotypic trait "extended shelf life".

The invention claimed is:

1. A method for producing a progeny *Cucumis sativus* plant, wherein the *Cucumis sativus* plant provides cucumber fruits exhibiting a phenotypic trait of extended shelf life, the method comprising the steps of:

(a) providing a first *Cucumis sativus* plant comprising at least one quantitative trait locus (QTL) associated with the phenotypic trait;

(b) crossing the first *Cucumis sativus* plant with a second *Cucumis sativus* plant to produce progeny *Cucumis sativus* plants;

(c) analyzing the progeny *Cucumis sativus* plants from the crossing for the at least one QTL; and (d) identifying and selecting progeny *Cucumis sativus* plants which produce fruits exhibiting extended shelf life, and contain the at least one QTL;

wherein the at least one QTL is selected from QTL1 or QTL2 and wherein;

QTL 1 is identified by a first molecular marker of about 66 base pairs consisting from 5' to 3' of a first primer having the nucleotide sequence having a first molecular marker sequence on one end and a second molecular marker sequence on the other wherein the first molecular marker binds a first primer sequence of SEQ ID No.: 1, a cucumber genomic fragment, and a second primer having the nucleotide sequence of SEQ ID No.: 2; and a second molecular marker of about 230 base pairs consisting from 5' to 3' of wherein the second molecular marker binds a first primer having the nucleotide sequence of SEQ ID No.: 3, a cucumber genomic fragment, and a second primer having the nucleotide sequence of SEQ ID No.: 4; and QTL 2 is identified by a first molecular marker of about 137 base pairs consisting from 5' to 3' of a first primer having the nucleotide a nulceotide sequence having a first molecular marker sequence on one end and a second molecular marker sequence on the other wherein the first molecular marker binds a first primer sequence of SEQ ID No.: 5, a cucumber genomic fragment, and a second primer having the nucleotide sequence of SEQ ID No.: 6; and a second molecular marker of about 230 base pairs consisting from 5' to 3' of wherein the second molecular marker binds a first primer sequence of SEQ ID No.: 7, a cucumber genomic fragment, and a second primer having the nucleotide sequence of SEQ ID No.: 8.

2. The method according to claim 1, wherein the at least one QTL is QTL1.

3. The method according to claim 2, wherein the at least one QTL1 comprises SEQ ID No: 9.

4. The method according to claim 1, wherein the progeny *Cucumis sativus* plant contains at least one QTL1 and at least one QTL2.

5. The method according to claim 1, wherein the phenotypic trait of extended shelf life extends the shelf life of a cucumber fruit by at least two, at least four, or at least six days as compared to the shelf life of a cucumber fruit that does not contain the at least one QTL, when stored under the same storage conditions.

6. The method according to claim 5, wherein the at least one QTL is QTL1.

7. The method according to claim 5, wherein the progeny *Cucumis sativus* plant contains at least one QTL1 and at least one QTL2.

8. The method according to claim 1, wherein the phenotypic trait of extended shelf life extends the shelf life of a cucumber fruit by at least eighteen, at least twenty, or at least twenty-two days as compared to the shelf life of a cucumber fruit that does not contain the at least one QTL, when stored under the same storage conditions.

9. The method according to claim 8, wherein the at least one QTL is QTL1.

10. The method according to claim 8, wherein the progeny Cucumis sativus plant contains at least one QTL1 and at least one QTL2.

11. A cucumber fruit of a progeny *Cucumis sativus* plant exhibiting a phenotypic trait of extended shelf life, wherein the progeny *Cucumis sativus* plant is produced by the method of claim 1.

12. The cucumber fruit of a progeny *Cucumis sativus* plant according to claim 11, wherein the at least one QTL is QTL1.

13. The cucumber fruit of a progeny *Cucumis sativus* plant according to claim 11, wherein the progeny *Cucumis sativus* plant contains at least one QTL1 and at least one QTL2.

* * * * *

SEQUENCE LISTING

```
<160> NUMBER OF SEQ ID NOS: 9

<210> SEQ ID NO 1
<211> LENGTH: 18
<212> TYPE: DNA
<213> ORGANISM: Artificial Sequence
<220> FEATURE:
<223> OTHER INFORMATION: Synthetic
```

```
<400> SEQUENCE: 1
gactgcgtac caattctt                                                    18

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
gatgagtcct gagtaacat                                                   19

<210> SEQ ID NO 3
<211> LENGTH: 18
<212> TYPE: DNA
<213> ORGANISM: Artificial Sequence
<220> FEATURE:
<223> OTHER INFORMATION: Synthetic

<400> SEQUENCE: 3
gactgcgtac caattccc                                                    18

<210> SEQ ID NO 4
<211> LENGTH: 19
<212> TYPE: DNA
<213> ORGANISM: Artificial Sequence
<220> FEATURE:
<223> OTHER INFORMATION: Synthetic

<400> SEQUENCE: 4
gatgagtcct gagtaacat                                                   19

<210> SEQ ID NO 5
<211> LENGTH: 18
<212> TYPE: DNA
<213> ORGANISM: Artificial Sequence
<220> FEATURE:
<223> OTHER INFORMATION: Synthetic

<400> SEQUENCE: 5
gactgcgtac caattcat                                                    18

<210> SEQ ID NO 6
<211> LENGTH: 19
<212> TYPE: DNA
<213> ORGANISM: Artificial Sequence
<220> FEATURE:
<223> OTHER INFORMATION: Synthetic

<400> SEQUENCE: 6
gatgagtcct gagtaacat                                                   19

<210> SEQ ID NO 7
<211> LENGTH: 18
<212> TYPE: DNA
<213> ORGANISM: Artificial Sequence
<220> FEATURE:
<223> OTHER INFORMATION: Synthetic

<400> SEQUENCE: 7
gactgcgtac caattcta                                                    18
```

```
<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
gatgagtcct gagtaacta                                                    19

<210> SEQ ID NO 9
<211> LENGTH: 395
<212> TYPE: DNA
<213> ORGANISM: Artificial Sequence
<220> FEATURE:
<223> OTHER INFORMATION: Synthetic

<400> SEQUENCE: 9
gataaccttc tttccaaggt ttgcactaat gtttctcttt tgcttgtaat tgatggttgc       60
ctctcttttt tattcttctc tttcttttt tggagggcc tgggatgagc aaatgtactt       120
ggtaatctga aaattttgag gaactaaaac taaagagcaa ttatcccttt ccacgaatac      180
ttttttttgc taaattctgg atctcttcat ggattttaac caaggaaata gttgtatcga      240
ttaattctta gtttacttta atccctcggc tattaattgc cactttaatg tctaaacaag      300
gaactaaatt agtcttagaa gttccatgta tcatatacat gaatgatgca ttaatagatc      360
tgttctctat attgtattgg aattggcgct ttttc                                 395
```